(12) United States Patent
Lee et al.

(10) Patent No.: US 11,338,282 B2
(45) Date of Patent: May 24, 2022

(54) TUBE ASSEMBLY FOR DRIPPING TO DIAGNOSTIC STRIP AND EXTRACTING GENE FRAGMENT

(71) Applicant: WELLS BIO, INC., Seoul (KR)

(72) Inventors: Min Jun Lee, Seoul (KR); Hyeon Seok Kim, Gyeonggi-do (KR); Young Ho Choi, Seoul (KR)

(73) Assignee: WELLS BIO, LLC, Seoul (KR)

( * ) Notice: Subject to any disclaimer, the term of this patent is extended or adjusted under 35 U.S.C. 154(b) by 0 days.

(21) Appl. No.: 16/609,777

(22) PCT Filed: Aug. 14, 2019

(86) PCT No.: PCT/KR2019/010362
§ 371 (c)(1),
(2) Date: Dec. 2, 2019

(87) PCT Pub. No.: WO2020/036435
PCT Pub. Date: Feb. 20, 2020

(65) Prior Publication Data
US 2021/0268493 A1    Sep. 2, 2021

(30) Foreign Application Priority Data

Aug. 17, 2018    (KR) ........................ 10-2018-0096203

(51) Int. Cl.
*B01L 3/02*    (2006.01)
*C12Q 1/6806*    (2018.01)

(52) U.S. Cl.
CPC .......... *B01L 3/0293* (2013.01); *C12Q 1/6806* (2013.01); *B01L 2200/06* (2013.01); *B01L 2300/0681* (2013.01); *B01L 2300/0832* (2013.01); *B01L 2300/123* (2013.01)

(58) Field of Classification Search
CPC ............... B01L 3/0293; B01L 2200/06; B01L 2300/0681; B01L 2300/0832; B01L 2300/123; C12Q 1/6808
See application file for complete search history.

(56) References Cited

U.S. PATENT DOCUMENTS 7,964,098 B2    6/2011    Williams

FOREIGN PATENT DOCUMENTS

| EP | 0073551 A2 | 3/1983 |
|---|---|---|
| JP | 2008093604 A | 4/2008 |
| KR | 101319606 | 10/2013 |
| KR | 101330605 | 11/2013 |
| WO | 2008097975 A1 | 8/2008 |

*Primary Examiner* — Christopher Adam Hixson
(74) *Attorney, Agent, or Firm* — Edwin S. Flores; Daniel J. Chalker; Chalker Flores, LLP

(57) ABSTRACT

The present invention relates to a tube assembly for dripping. According to an embodiment, a tube assembly for dripping includes a tube (100) having a hole (H) at an upper portion thereof, and a filter tip (200) having a tip (210) including, an insertion part (211) inserted into the hole (H) of the tube (100) and, an expansion part (212) connected to the insertion part (211) and having a diameter that is larger than that of the hole (H), and a discharge pipe (213) connected to the expansion part (212) and acting as a passage, through which a solution (S) stored in the interior of the tube (100) is discharged, wherein a discharge adjusting part (213a) having a discharge hole (h) having a predetermined diameter (d1) is formed in the interior of the discharge pipe (213) that is spaced apart from a lower end of the discharge pipe (213) by a predetermined distance.

9 Claims, 5 Drawing Sheets

TUBE ASSEMBLY FOR DRIPPING TO DIAGNOSTIC STRIP AND EXTRACTING GENE FRAGMENT

TECHNICAL FIELD OF THE INVENTION

The present invention relates to a tube assembly for dripping a sample on a diagnostic strip and extracting a gene fragment.

BACKGROUND OF THE INVENTION

A prompt immunity diagnosis kit refers to a kit that may simply diagnose diseases and cause materials thereof in a short time with immunochromatography by using body fluid such as blood, urine, or nasal discharges. The immunochromatography is an inspection method in which immunochemistry and chromatography are combined, and is an inspection method that applies a unique immunity reactivity of an antibody against an antigen, coloring characteristics of colloidal gold, and mobility of molecules by the capillary phenomenon of a porous membrane. The prompt immunity diagnosis kit using immunochromatography is used in various fields of diagnosis kits in an aspect that an inspection result can be determined easily and rapidly, and a flu diagnosis kits pertains to the prompt immunity diagnosis kit.

In the analysis using the diagnosis kit, it is important to load a predetermined amount of a sample on a sample pad of the diagnosis kit. When a sample corresponding to an amount that is smaller or larger than the predetermined amount, an inaccurate diagnosis result is caused.

Although various tubes for dripping a sample on a diagnosis kit have been developed, the tube includes a rather rigid material, making it difficult to load the sample, the sample is dripped in the form of water streams because the size of the discharge hole is too larger or small, or the sample in the interior of the tube can be discharged only when a strong force is applied.

Generally, in order to perform diagnosis of molecules that pertains to in vitro diagnostics, a process of extracting genes of a sample of a patient, who is to be inspected, is accompanied. To achieve this, the following complex processes are performed, and pure DNAs or RNAs can be acquired through processes such as lysis, binding, washing, elution, and the extracted samples are used as samples of various amplification methods such as polymerase chain reaction (PCR), loop mediated amplification (LMAP), rolling circle amplification (RCA), ligase chain reaction (LCR), and recombinase polymerase amplification (RPA).

However, for diagnosis of molecules, the processes are complex and expert manpower is necessary, and much time is consumed.

(Patent document 1) Japanese Patent Application Publication No. 2008-093604 (Apr. 24, 2008)

(Patent document 2) Korean Patent No. 10-1319606 (Oct. 11, 2013)

DETAILED DESCRIPTION OF THE INVENTION

Technical Problem

The present invention relates to a tube assembly in which the size of a discharge hole and the length of a discharge pipe are determined such that a predetermined amount of a sample can be loaded on a diagnosis kit.

The present invention also relates to a tube assembly, by which molecules of a sample can be simply diagnosed after the sample is only dissolved and a molecule diagnosis device after cell debris is filtered.

Technical Solution

According to an embodiment, a tube assembly for dripping including a tube 100 having a hole H at an upper portion thereof, and a filter tip 200 having a tip 210 including an insertion part 211 inserted into the hole H of the tube 100 and, an expansion part 212 connected to the insertion part 211 and having a diameter that is larger than that of the hole H, and a discharge pipe 213 connected to the expansion part 212 and acting as a passage, through which a solution S stored in the interior of the tube 100 is discharged, wherein a discharge adjusting part 213a having a discharge hole h having a predetermined diameter d1 is formed in the interior of the discharge pipe 213 that is spaced apart from a lower end of the discharge pipe 213 by a predetermined distance.

According to an embodiment, a value obtained by dividing a distance d2 from the lower end of the discharge pipe 213) to the discharge adjusting part 213a by the diameter d1 of the discharge hole h may be 3.2 to 4.8.

According to an embodiment, the diameter d1 of the discharge hole h may be 1.377 mm to 1.683 mm.

According to an embodiment, the distance d2 from the lower end of the discharge pipe 213 to the discharge adjusting part 213a may be 5.4 mm to 6.6 mm, and the inner diameter of the discharge pipe 213 may be 4.0005 mm to 4.894 mm.

According to an embodiment, the filter 200 and a fixing ring 230 for fixing the filter 220 may be installed in the interior of the insertion part 211.

According to an embodiment, the outer diameter of the insertion part 211 may be the same as the inner diameter of the hole H.

According to an embodiment, the hole H of the tube 100 may be covered by a sealing cover 110 when the tube assembly is not used, and the tube 100 may be assembled with the filter tip 200 only when the tube assembly is used.

According to an embodiment, the tube 100 may include a flexible material.

According to an embodiment, the tube 100 may include a material that is not melt at a temperature of 90° C. to 100° C.

Advantageous Effects

When the present invention is compared with the conventional tube, from which a sample is dripped in the form of water streams or from which a sample is dripped only when a strong force is applied, a predetermined amount of a sample that is necessary for a diagnosis kit can be dripped in the form of water drops, thus enhancing the precision and reliability of the diagnosis result that appears in the diagnosis kit.

Further, the tube 100 is formed of a flexible material, and the sample can be dripped relatively easily.

Further, the filter tip 200 is insertion-coupled to the tube 100, and thus the problem of the solution S in the interior of the tube 100 evaporates to the outside due to the conventional screw-coupling can be solved.

Further, because the filter 220 is located in the filter tip 220, a problem of the solid materials included in the solution S and the like blocking the discharge hole h can be prevented.

Further, because the specific ratio of the diameter d1 of the discharge hole h to the distance between the lower end of the discharge pipe 213 and the discharge adjusting part 213a is determined, a predetermined amount of the solution S can be dripped to the outside while the filter tip 220 is not separated from the tube 100 by the pressure formed in the interior of the tube 100 when the tube 100 is pressed.

Further, impurities that may be generated when genes such as DNAs or RNAs are extracted through lyses due to use of the filter tip 200 and hampers reactions can be removed.

Further, because cells are dissolved and filtered by one tube at the same time, various contamination problems that may occur in a complex gene single piece extracting process can be prevented.

BEST MODE

Hereinafter, a tube assembly for dripping a diagnosis strip according to an embodiment of the present invention will be described in detail with reference to the accompanying drawings.

Figure 1:
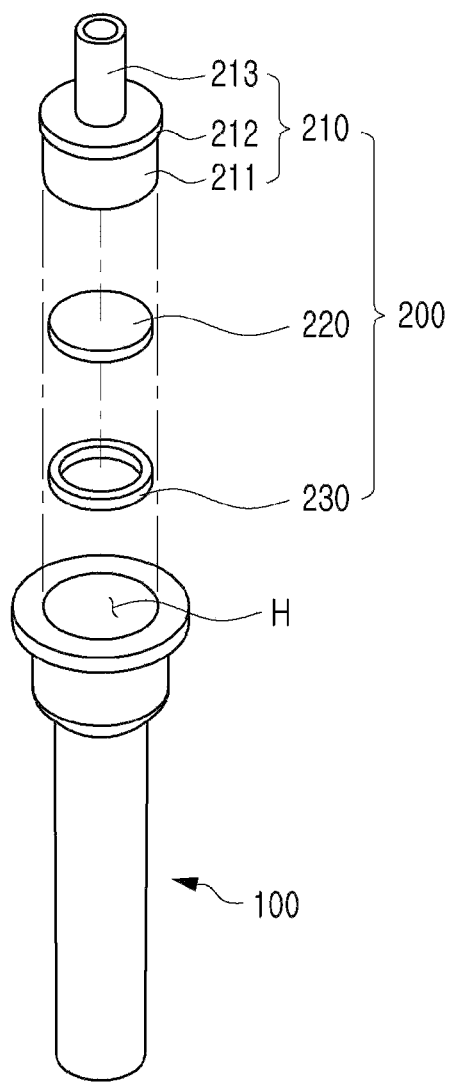
FIG. 1 is an exploded perspective view of a tube assembly for dripping according to an embodiment of the present invention.

Referring to FIG. 1, the tube assembly for dripping a diagnosis strip according to an embodiment of the present invention includes a tube 100 and a filter tip 200.

The tube 100 may include a tubular shape, and a hole H for coupled to the filter tip 200 is formed at an upper portion thereof. The tube 100 is sealed by a sealing cover 110 that covers an upper portion thereof when the tube assembly is not used. The sealing cover 110 is removed to load a sample in a diagnosis kit, and a detection material is extracted from or dissolved in a solution S by introducing a collection rod (for example, a cotton rod), to which the detection material is stuck.

Further, the tube 100 may be formed of a flexible material, and accordingly, an extraction liquid S in the interior of the tube 100 may be easily discharged to the outside when the tube 100 is pressed. In detail, it is preferable that the tube 100 includes a material that is not melt at a temperature of 90° C. to 100° C., in more detail, a temperature of 95° C., at which the tube 100 is generally not dissolved.

The filter tip 200 is a part which is inserted into a hole H of the tube 100 and through which the solution S stored in the interior of the tube 100 is discharged through the filter tip 200.

Figure 2:
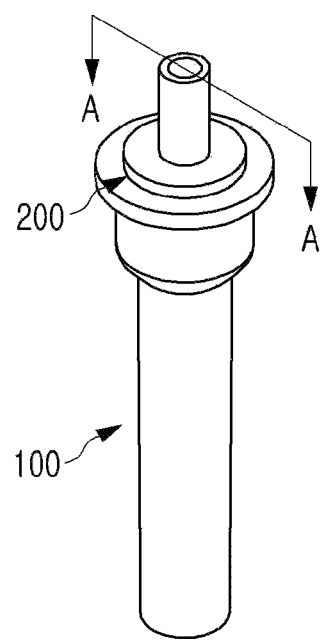
FIG. 2 is a perspective view the tube assembly for dripping of FIG. 1 in a coupled state.
Figure 3:
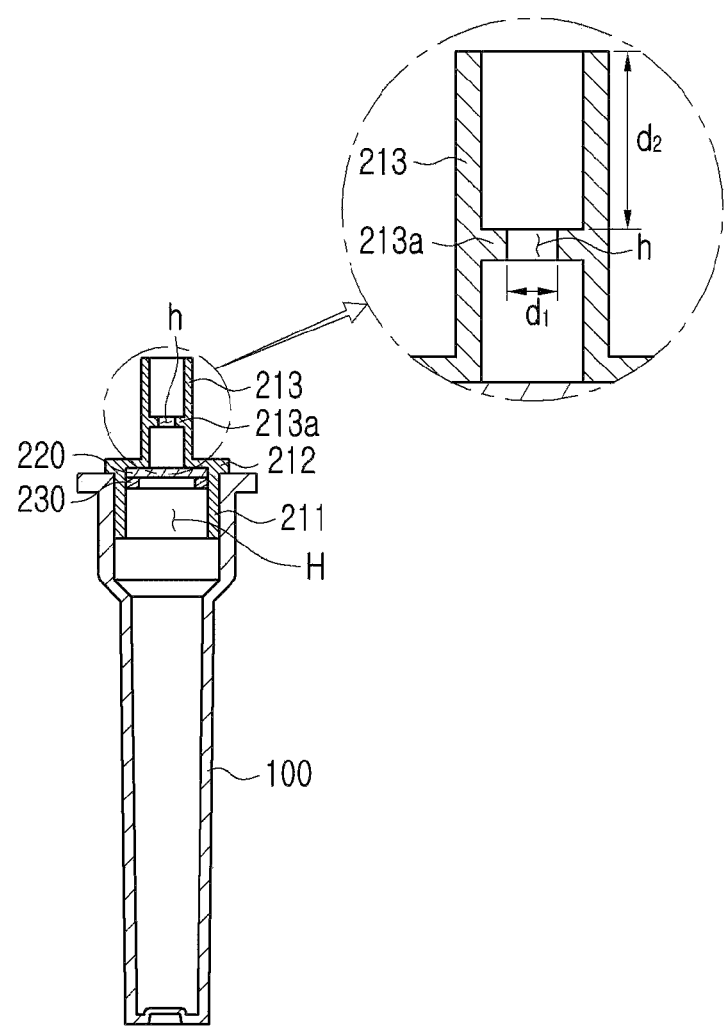
FIG. 3 is a cross-sectional view taken along a line A-A of FIG. 2.
Figure 4A:
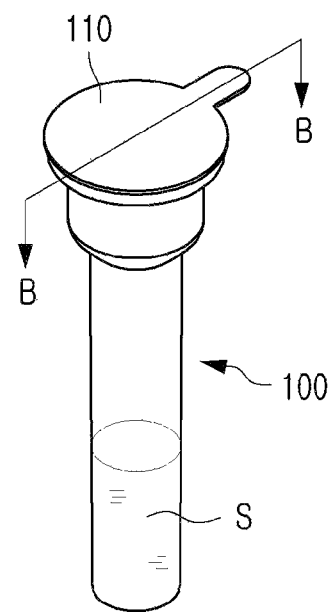
FIGS. 4A and 4B are views illustrating a tube, an upper side of which is covered by a sealing cover 110.
Figure 4B:
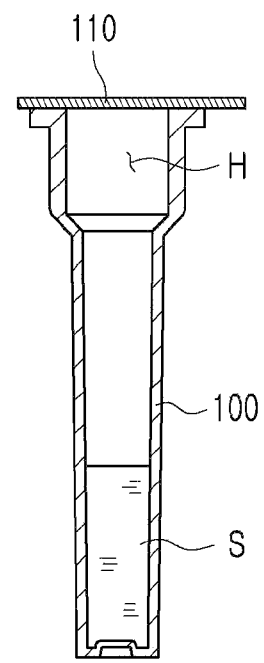

Referring to FIG. 2, the filter tip 200 may include a tip 210, a filter 220, and a fixing ring 230.

The tip 210 includes an insertion part 211, an expansion part 212, and a discharge pipe 213.

The insertion part 211 is a part that is inserted into the hole H of the tube 100, and it is preferable that the outer diameter of the insertion part 211 is the same as the inner diameter of the hole H not to be separated from the tube 100 after the insertion. The insertion part 211 is insertion-coupled to the hole H instead of being screw-coupled to the hole H, and by employing the insertion coupling, a problems that the solution S in the tube S may vaporize to the outside in the screw-coupling can be solved.

The expansion part 212 is connected to the insertion part 211 and has a diameter that is larger than that of the hole H, and is a part that restricts the depth of insertion of the insertion part 211 into the hole H and more completely covers the hole H.

The discharge pipe 213 includes a tubular shape and is connected the expansion part 212, and the solution S in the interior of the tube 100 is discharged to the outside through the discharge pipe 213.

A discharge adjusting part 231a protrudes from an inner surface of the discharge pipe 213 circumferentially at a location that is spaced apart from the lower end of the discharge pipe 213 by a predetermined distance d2 in the interior of the discharge pipe 213. Accordingly, a discharge hole h having a predetermined diameter d1 is formed at the center of the discharge adjusting part 213a, and the amount of the extraction liquid S discharged to the outside of the discharge pipe 213 may be adjusted by adjusting the diameter d1 of the discharge hole h and the distance d2, by which the discharge adjusting part 213a is spaced apart from the lower end of the discharge pipe 213.

That is, the solution S stored in the interior of the tube 100 is discharged through a passage in the interior of the discharge pipe 213, and an amount of the solution S corresponding to the volume of the space between the lower end of the discharge pipe 213 and the discharge adjusting part 213a is discharged to the outside. This is due to the principle in which the solution S is stored in the space by the volume due to the surface tension of the liquid and then is discharged.

In order to discharge the solution S to the outside in the form of water drops, the present invention was designed such that the ratio of the distance from the lower end of the discharge pipe 213 to the discharge adjusting part 213a to the diameter d1 of the discharge hole h is 3.2 to 4.8. In more detail, the diameter d1 of the discharge hole h may be 1.377 mm to 1.683 mm, and in more detail, may be 1.53 mm. Further, the distance d2 from the lower end of the discharge pipe 213 to the discharge adjusting part 213a may be 5.4 mm to 6.6 mm, and in more detail, may be 6 mm. Further, the inner diameter of the discharge pipe 213 may be 4.005 mm to 4.895 mm, and in more detail, may be 4.45 mm.

The filter 220 and the fixing ring 230 are installed in the interior of the insertion part 211.

The filter 220 is a part that filters materials, such as solid materials included in the solution S, which are unnecessary for analysis of a diagnosis kit, and the fixing ring 230 is a part that is located at an upper portion of the filter 220 to fix the filter 220 such that the filter 220 is not separated. Because the filter 220 is located in the filter tip 200, a problem of the solid materials included in the solution S and the like blocking the discharge hole h can be prevented.

Hereinafter, a method for using the tube assembly for dripping a diagnosis strip according to an embodiment of the present invention will be described in detail with reference to FIG. 5.

Further, the collection rod (for example, a cotton rod) is introduced into a nasal cavity or an oral cavity of a subject, and a detection material, such as nasal discharges or saliva. In addition to the nasal discharges or saliva, the detection materials, such as blood or stool may be applied.

Next, the sealing cover 110 at an upper end of the tube 100 is removed from the tube 100.

Next, the detection material stuck to the collection rod is extracted from the solution S in the interior of the tube 100 by inserting the collection rod into the tube 100.

Next, the filter tip 200 is inserted into the hole H of the tube 100, and is turned over such that the discharge pipe 213 faces the lower side.

Next, the discharge pipe 213 is located at an upper portion of the sample pad of the diagnosis kit, and the solution S, the amount of which is suitable for the corresponding diagnosis kit, is dripped by applying a force to the tube 100 of the flexible material.

Finally, a diagnosis result is acquired by observing a change result of an inspection ray and a comparative ray.

Hereinafter, a method for using the tube assembly for extracting a sample for diagnosing molecules according to an embodiment of the present invention will be described in detail with reference to FIG. 5.

Further, the collection rod (for example, a cotton rod) is introduced into a nasal cavity or an oral cavity of a subject, and a detection material, such as nasal discharges or saliva, is collected. In addition to the nasal discharges or saliva, the detection materials, such as blood or stool may be applied.

Next, the sealing cover 110 at an upper end of the tube 100 is removed from the tube 100.

Next, the detection material stuck to the collection rod is extracted or dissolved from the solution S in the interior of the tube 100 by inserting the collection rod into the tube 100.

Next, the tube 100 in which the solution and the detection material are heated for two to ten minutes by a heating block such that cells are completely dissolved.

Next, the filter tip 200 is inserted into the hole H of the tube 100, and is turned over such that the discharge pipe 213 faces the lower side.

Next, the solution S, the amount of which is suitable for the corresponding diagnosis kit, is mixed with a molecule diagnosis sample, which has been prepared in advance, by applying a force to the tube 100 of the flexible material.

Figure 5:
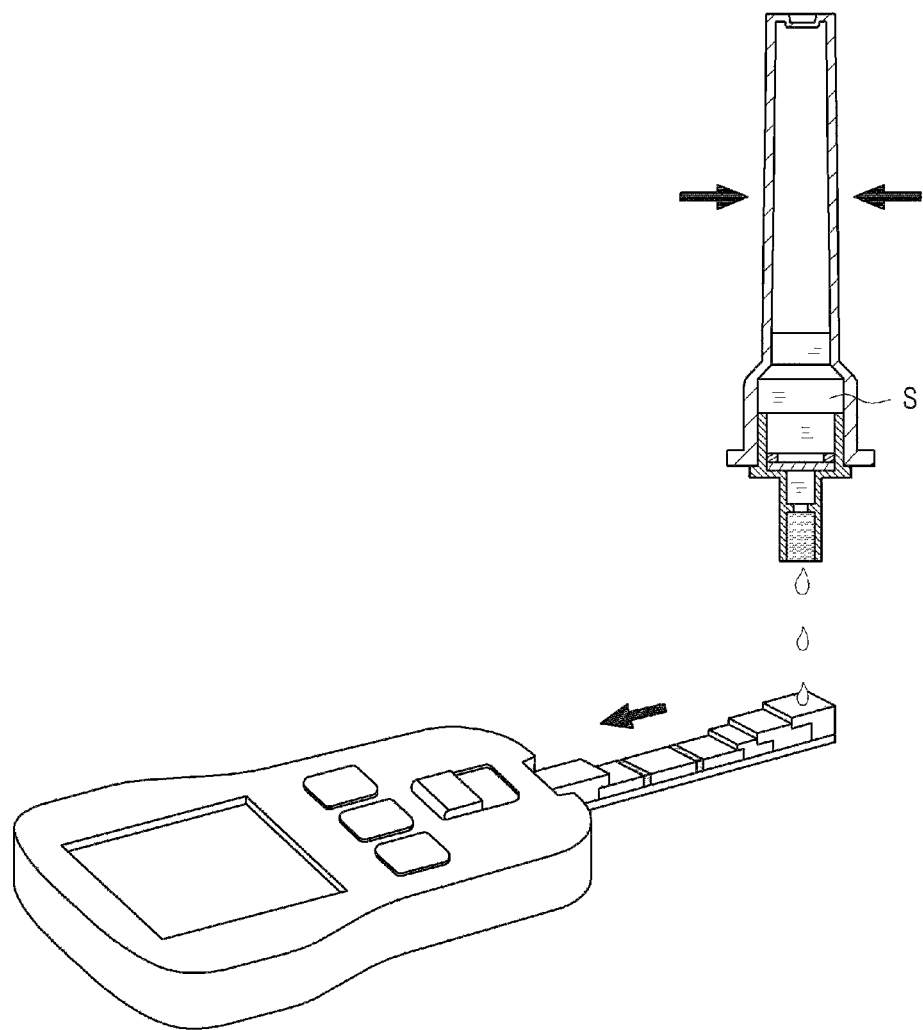
FIG. 5 is a view illustrating a use state of the tube assembly for dripping according to the embodiment of the present invention.

Finally, a diagnosis result is acquired by loading molecule diagnosis equipment (FIG. 5).

When the present invention is compared with the conventional tube, from which a sample is dripped in the form of water streams or from which a sample is dripped only when a strong force is applied, a predetermined amount of a sample that is necessary for a diagnosis kit can be dripped in the form of water drops, thus enhancing the precision and reliability of the diagnosis result that appears in the diagnosis kit.

Further, the tube 100 is formed of a flexible material, and the sample can be dripped relatively easily.

Further, the filter tip 200 is insertion-coupled to the tube 100, and thus the problem of the extraction liquid S in the interior of the tube 100 evaporates to the outside due to the conventional screw-coupling can be solved.

Further, because the filter 220 is located in the filter tip 200, a problem of the solid materials included in the solution S and the like blocking the discharge hole h can be prevented.

Further, because the specific ratio of the diameter d1 of the discharge hole h to the distance between the lower end of the discharge pipe 213 and the discharge adjusting part 213a is determined, a predetermined amount of the solution S can be dripped to the outside while the filter tip 200 is not separated from the tube 100 by the pressure formed in the interior of the tube 100 when the tube 100 is pressed.

Further, impurities that may be generated when genes such as DNAs or RNAs are extracted through lyses due to use of the filter tip 200 and hampers reactions can be removed.

Further, because cells are dissolved and filtered by one tube at the same time, various contamination problems that may occur in a complex gene fragment extracting process can be prevented.

Although the embodiment of the present invention illustrated in the drawings has been described so that those skilled in the art can easily reproduce and implement the present invention, it is merely exemplary and it will be understood by those skilled in the art that various modifications and equivalent embodiments can be made. Therefore, the scope of the present invention should be determined according to the claims.

DESCRIPTION OF REFERENCE NUMERALS

100: tube
110: sealing cover
200: filter tip
210: tip
211: insertion part
212: expansion part
213: discharge pipe
220: filter
230: fixing ring

What is claimed is:

1. A tube assembly for dripping comprising:
a tube (100) having a hole (H) at an upper portion thereof; and
a filter tip (200) having a tip (210) comprising:
an insertion part (211) inserted into the hole (H) of the tube (100);
an expansion part (212) connected to the insertion part (211) and having a diameter that is larger than that of the hole (H); and
a discharge pipe (213) connected to the expansion part (212) and acting as a passage, through which a solution (S) stored in the interior of the tube (100) is discharged,
wherein a discharge adjusting part (213a) having a discharge hole (h) having a predetermined diameter (d1) is formed in the interior of the discharge pipe (213) that is spaced apart from a lower end of the discharge pipe (213) by a predetermined distance.

2. The tube assembly for dripping of claim 1, wherein a value obtained by dividing a distance (d2) from the lower end of the discharge pipe (213) to the discharge adjusting part (213a) by the diameter (d1) of the discharge hole (h) is 3.2 to 4.8.

3. The tube assembly for dripping of claim 2, wherein the diameter (d1) of the discharge hole (h) is 1.377 mm to 1.683 mm.

4. The tube assembly for dripping of claim 3, wherein the distance (d2) from the lower end of the discharge pipe (213) to the discharge adjusting part (213a) is 5.4 mm to 6.6 mm, and the inner diameter of the discharge pipe (213) is 4.0005 mm to 4.895 mm.

5. The tube assembly for dripping of claim 4, wherein the filter (200) and a fixing ring (230) for fixing the filter (220) are installed in the interior of the insertion part (211).

6. The tube assembly for dripping of claim 4, wherein the outer diameter of the insertion part (211) is the same as the inner diameter of the hole (H).

7. The tube assembly for dripping of claim 4, wherein the hole (H) of the tube (100) is covered by a sealing cover (110)

when the tube assembly is not used, and the tube (100) is assembled with the filter tip (200) only when the tube assembly is used.

8. The tube assembly for dripping of claim 4, wherein the tube (100) comprises a flexible material.

9. The tube assembly for dripping of claim 8, wherein the tube (100) comprises a material that is not melt at a temperature of 90° C. to 100° C.

* * * * *